(12) United States Patent
Parks, II et al.

(10) Patent No.: US 9,000,374 B2
(45) Date of Patent: Apr. 7, 2015

(54) EGR DISTRIBUTION AND FLUCTUATION PROBE BASED ON $CO_2$ MEASUREMENTS

(71) Applicant: UT-Battelle LLC, Oak Ridge, TN (US)

(72) Inventors: James E. Parks, II, Knoxville, TN (US); William P. Partridge, Jr., Oak Ridge, TN (US); Ji Hyung Yoo, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 76 days.

(21) Appl. No.: 13/912,462

(22) Filed: Jun. 7, 2013

(65) Prior Publication Data

US 2013/0327943 A1  Dec. 12, 2013

Related U.S. Application Data

(60) Provisional application No. 61/657,205, filed on Jun. 8, 2012.

(51) Int. Cl.
*G01N 21/59* (2006.01)
*G01N 21/3504* (2014.01)

(52) U.S. Cl.
CPC ............ *G01N 21/59* (2013.01); *G01N 21/3504* (2013.01)

(58) Field of Classification Search
CPC .......................... G01N 21/3504; G01N 21/59
USPC ............. 250/339.01, 339.06, 339.07, 339.13, 250/343; 356/436, 437
See application file for complete search history.

(56) References Cited

U.S. PATENT DOCUMENTS

| | | | |
|---|---|---|---|
| 5,373,367 | A | 12/1994 | DeGunther et al. |
| 5,751,423 | A | 5/1998 | Traina et al. |
| 5,831,730 | A | 11/1998 | Traina et al. |
| 5,999,257 | A | 12/1999 | Myers et al. |

(Continued)

FOREIGN PATENT DOCUMENTS

JP  5898652  6/1983

OTHER PUBLICATIONS

Michael Cundy, Torsten Schucht, Olaf Thiele, and Volker Sick, High-speed laser-induced fluorescence and spark plug absorption sensor diagnostics for mixing and combustion studies in engines, Applied Optics, vol. 48, No. 4 / Feb. 1, 2009.

(Continued)

*Primary Examiner* — Mark R Gaworecki
(74) *Attorney, Agent, or Firm* — Warner Norcross & Judd LLP

(57) ABSTRACT

A diagnostic system having a single-port EGR probe and a method for using the same. The system includes a light source, an EGR probe, a detector and a processor. The light source may provide a combined light beam composed of light from a mid-infrared signal source and a mid-infrared reference source. The signal source may be centered at 4.2 μm and the reference source may be centered at 3.8 μm. The EGR probe may be a single-port probe with internal optics and a sampling chamber with two flow cells arranged along the light path in series. The optics may include a lens for focusing the light beam and a mirror for reflecting the light beam received from a pitch optical cable to a catch optical cable. The signal and reference sources are modulated at different frequencies, thereby allowing them to be separated and the signal normalized by the processor.

16 Claims, 7 Drawing Sheets

(56) References Cited

U.S. PATENT DOCUMENTS

| | | |
|---|---|---|
| 6,744,059 B2 | 6/2004 | DiDomenico et al. |
| 6,744,516 B2 | 6/2004 | DiDomenico et al. |
| 6,833,922 B2 | 12/2004 | DiDomenico et al. |
| 7,301,641 B1 | 11/2007 | Overby et al. |
| 7,839,492 B2 | 11/2010 | Parks, II et al. |
| 7,884,937 B2 * | 2/2011 | Prasad et al. .................. 356/437 |
| 2004/0263851 A1 * | 12/2004 | Dobbs et al. .................. 356/436 |

OTHER PUBLICATIONS

C. Schulz, Advanced Laser Imaging Diagnostics in Combustion, Z. Phys. Chem. 219 (2005) pp. 509-554.

* cited by examiner

EGR DISTRIBUTION AND FLUCTUATION PROBE BASED ON $CO_2$ MEMOS

EGR DISTRIBUTION AND FLUCTUATION PROBE BASED ON $CO_2$ MEASUREMENTS

CROSS REFERENCE TO RELATED APPLICATIONS

This application claims the benefit of U.S. Provisional Application No. 61/657,205, filed Jun. 8, 2012. U.S. Provisional Application No. 61/657,205 is incorporated herein by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND OF THE INVENTION

The present invention relates to internal combustion engine diagnostics and more specifically to apparatuses and methods for determining the spatial and temporal nonuniformities of $CO_2$ in an intake fluid stream.

Internal combustion engines typically suffer from the ability to produce undesirable $NO_X$ emissions. Experience has revealed that more $NO_X$ emissions are formed at higher combustion temperatures and that $NO_X$ formation has a nonlinear dependence on temperature. More specifically, lowering the combustion temperature a little can result in relatively large reductions in $NO_X$ formation.

Exhaust-gas recirculation, EGR, is a technology used to reduce automotive $NO_X$ emissions, and which involves mixing some of the engine exhaust with the intake air. The exhaust gas acts as a diluent in the inlet air that reduces peak combustion temperature. Ideally, the air/exhaust mixture, or EGR fraction, is uniform across the various cylinders of a multi-cylinder engine. However, practically the EGR fraction can vary from cylinder to cylinder and cycle to cycle due to various spatial and temporal nonuniformities; e.g., non-ideal mixing, intake-manifold restrictions, and overlap of valve events with manifold resonating. Such nonuniformities can cause one cylinder to reach a limit (e.g., incomplete combustion, etc.) earlier than the other cylinders, and can limit the performance of the other cylinders. Ultimately, the result is lost efficiency and increased engine emissions.

An EGR probe that can be used to identify non-uniformities, track their origins and assess mitigation strategies could be a powerful tool for optimizing efficiency and performance of multi-cylinder engines. For example, a probe of this nature may be capable of identifying spatial or temporal fluctuations in the performance of the EGR system, which may result from the design or configuration of the EGR system, the intake manifold, engine events or other factors.

In the past, EGR probes that rely on capillary action have been developed to assist in mapping $CO_2$ variations within an engine intake manifold. These tiny capillary probes allow samples to be extracted from the intake manifold and delivered to remote equipment for analysis. The capillary probes are capable of being spatially translated so that they can take samples from different location within the exhaust manifold. For example, the capillary probes are capable of being mounted in different apertures in the intake manifold and of being inserted to different depths within a given aperture. The samples extracted using capillary probes are analyzed remotely using absorption spectroscopy or mass spectrometry, or other analytical technique, to determine $CO_2$ concentration. Although a meaningful advance, conventional capillary probes suffer from a variety of disadvantages. Perhaps most notably, capillary-probe-based diagnostic systems are not fast enough to measure fast valve-time scale, crank-angle variations. As a result, the use of capillary probes can place significant limitations on the capabilities the diagnostic system.

Another technique previously used to measure EGR fraction variations by cylinder is the use of oxygen sensors. Exhaust oxygen sensors are common on engines for vehicles and aid the engine system in controlling the air-to-fuel ratio during combustion. They function based on a solid state electrochemical cell (normally composed of a metal oxide). For the application of measuring EGR fraction distribution, they have limitations related to diffusion, temperature, and pressure. Gas measurement required diffusion into the electrochemical cell and also through a protective porous housing (commonly ceramic based); the time required for the diffusion process can limit temporal response especially relative to rapid cycle-to-cycle time scales. Also, the oxygen sensors must be heated to work effectively, and cool intake gas temperatures pose problems for the sensors to maintain the necessary sensor temperature. Lastly, variations in pressure in the intake system (often occurring especially for boosted engines) can alter oxygen sensor measurements.

SUMMARY OF THE INVENTION

The present invention provides an EGR probe capable of providing rapid and accurate measurement of $CO_2$ concentrations in a fluid stream, such as an engine intake manifold, intake runner or engine exhaust manifold. In one embodiment, the EGR probe is operatively coupled with a combined light source (a signal light source and a reference light source), a detector and a processor to provide a diagnostic system. The EGR probe of this embodiment includes a pitch optical cable (e.g., a hollow wave guide) that receives the light beam from the combined light source, a lens for focusing the light beam, a sampling chamber where the light beam passes through the fluid stream and a catch optical cable for conveying the light beam to the detector after it has passed through the sampling chamber. In one embodiment, the processor is configured to analyze the detector readings to determine $CO_2$ concentration within the fluid stream.

In one embodiment, the signal light source and the reference light source are driven at different operating frequencies (e.g., 50 kHz and 77 kHz), and the two corresponding signal components are separated from the detector readings by the processor using a Fourier transform or other suitable method. This allows the use of a single detector for both the signal light source and the reference light source.

In one embodiment, the light sources may produce light output in the mid-infrared (MIR) range. The combined light source may, for example, include a first light source centered at 4.2 μm and a second light source centered at 3.8 μm. The light sources may be light-emitting diodes. The system may also include separate filters for filtering the output of the two light sources to the desired spectral ranges, as well as a beam combiner for combining the filtered light from the two light sources into a single beam of light.

In one embodiment, the EGR probe may include a sampling chamber having two flow cells. The flow cells may be arranged in series and, if desired, may be separated by the lens. In this embodiment, the EGR probe may include a window that is disposed between the end of the pitch optical cable and the first flow cell. The window may be a collimator or other type of lens, if desired. The number of flow cells may vary from application to application.

In one embodiment, the EGR probe may include a mirror. The mirror may be disposed adjacent to the interior end of the probe to reflect the light beam from the pitch optical cable to the catch optical cable. The mirror may receive the light beam after it has passed from the pitch optical cable through the two flow cells and may reflect that light beam back through the two flow cells to the catch optical cable. As a result, the light beam may pass through each flow cell twice, thereby enhancing the absorption.

In one embodiment, the EGR probe is a single-port probe that is capable of being mounted in a single opening. The pitch optical cable and catch optical cable may be disposed adjacent to one another within a shared housing. The pitch cable may deliver light to the probe through a first end where it passes through the window, the first flow cell, the lens and the second flow cell to the second end. The mirror may be positioned at the second end and may reflect the light beam back toward the first end causing it to pass back through the second flow cell, the lens, the first flow cell, the window and into the catch optical cable. The catch optical cable may convey the reflected light beam back out of the first end of the probe to deliver it to the detector.

The processor may be connected to the output of the detector. The processor may be configured to separate the detector readings (or measurements) into a signal component and a reference component. The detector readings may be separated using a Fourier transform or other suitable method. The processor may also be configured to normalize the signal component as a function of the reference component using conventional normalization methods. Additionally, the processor may be configured to determine $CO_2$ concentration as a function of the normalized signal component.

In another aspect, the present invention provides a method for measuring spatial and temporal EGR fluctuations using an optical probe. The method generally includes the steps of: (a) providing an EGR probe in which portions of the pitch and catch optical path are includes in a single housing suitable for mounting within a single port, (b) producing first and second light beams with light over different spectra, (c) combining the first and second light beams into a combined light beam, (d) directing the combined light beam in a first direction through the housing via a pitch cable, (e) passing the combined light beam from the pitch cable through a fluid stream, for example, through a portion of the intake or exhaust manifold, (f) reflecting the combined light toward a catch cable, (g) directing the reflected beam through the housing in a direction opposite to the first direction via a catch cable, (h) receiving the light beam at a detector, and (i) determining the concentration of a component within the intake or exhaust manifold as function of the detected light beam. The step of determining the concentration of the component may include separating the detector output into signal and reference components, normalizing the signal component as a function of the reference component, and determining the concentration as a function of the normalized signal component.

The present invention provides a relatively simple diagnostic probe that is broadly applicable and suitable for use in applications with relatively severe packaging limitations. The EGR probe provides for the rapid processing of samples. As a result, the probe is capable of expanding development barriers. The use of a combined light source allows both signal and reference light beams to communicated through the probe using a single set of pitch and catch optics. Further, the combined light source allows the use of a single detector. The use of MIR LEDs provides a simple and cost effective combined light source that has appropriate absorption features for $CO_2$. The use of hollow wave guides provides a mechanism for conveying MIR light without unacceptable losses. The present invention may provide a diagnostic system that is capable of producing the data necessary to achieve efficiency, durability and emissions targets for advanced engine systems, particularly those using high EGR.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION OF THE CURRENT EMBODIMENT

Overview.

Figure 1:
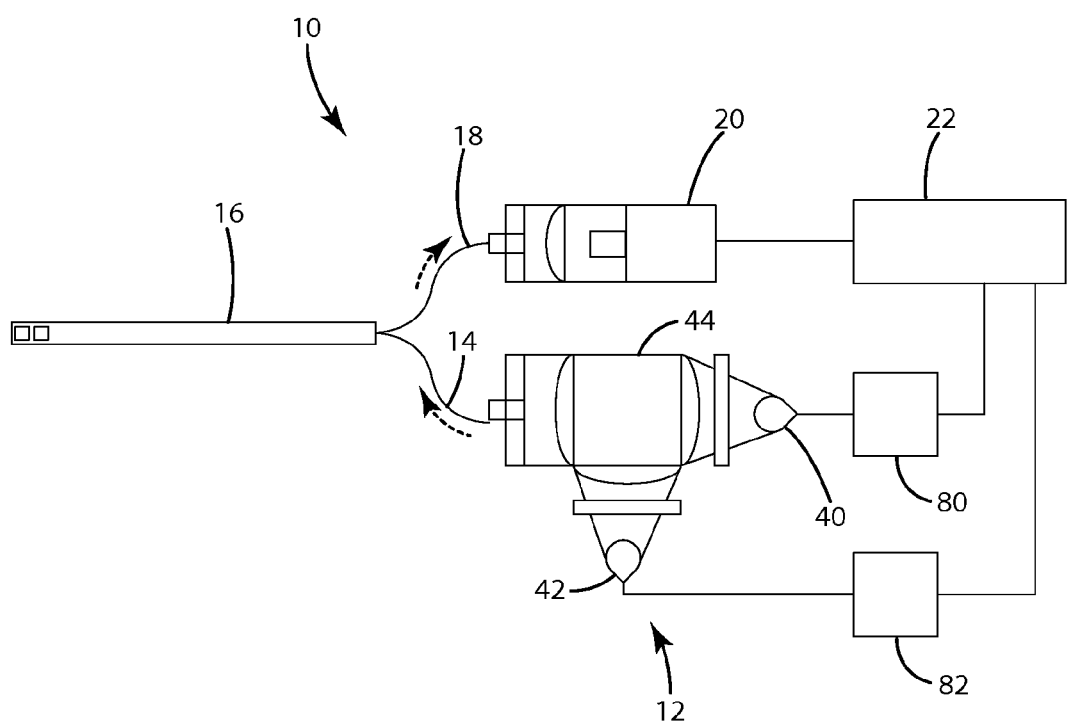
FIG. 1 is a schematic representation of a diagnostic system in accordance with an embodiment of the present invention.

A diagnostic system in accordance with an embodiment of the present invention is shown in FIG. 1 and generally designated 10. The diagnostic system 10 of this embodiment permits accurate measurement of $CO_2$ concentrations, and potentially other substances, within a fluid stream using absorption spectroscopy. The diagnostic system 10 generally includes a light source 12, a pitch optical cable 14, an EGR probe 16, a catch optical cable 18, a detector 20 and a processor 22 for determining $CO_2$ concentration based on the output of the detector 20. The light source 12 may be a mid-infrared (MIR) light source having a signal source 40 and a reference source 42 that are combined into a single light beam. In use, the reference source 42 is used to normalize the measurements from the signal source 40. The EGR probe 16 of this embodiment is a single-port probe capable of being installed in a single opening, such as in an aperture in an intake manifold I or an exhaust manifold (not shown).

The diagnostic system 10 may be used to measure $CO_2$ concentrations in essentially any application. In the illustrated embodiment, the diagnostic system 10 is used to measure $CO_2$ concentrations within an engine intake manifold I to determine the spatial and temporal non-uniformities of $CO_2$ in the fluid stream. For example, the system 10 may be used to measure cylinder-to-cylinder and cycle-to-cycle EGR fluctuations. In the context of engines with exhaust gas redistribution (EGR), the diagnostic system 10 may be used to quantify intake EGR fluctuations using $CO_2$ measurements.

For purposes of disclosure, the present invention is described in connection with a diagnostic system 10 used with an intake manifold I for an internal combustion engine (not shown) having an exhaust gas recirculation (EGR) system (not shown). In this context, the present invention can be used to assess spatial and temporal fluctuations in exhaust gas based on measurement of $CO_2$ concentration. The data collected by the diagnostic system 10 may be used to refine the EGR system, the intake manifold I, engine control parameters or other characteristics to improve performance of the engine and minimize $NO_X$ production. Although disclosed in the context of an EGR diagnostic system, the present invention may be readily adapted for use in other types of diagnostics. For example, the system 10 may allow diagnostics relating to other engine characteristics that can be assessed using $CO_2$ concentration. The diagnostic system 10 may also be used for applications that do not involve engines. The system may be modified to measure substances other than $CO_2$. For example, the light source, detector and processor may be modified to measure other substances, and provide diagnostics based on those substances can be performed.

Construction.

Figure 9:
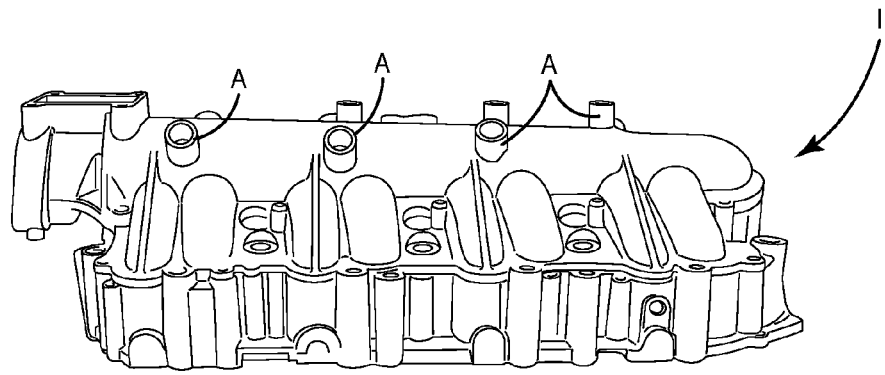
FIG. 9 is a perspective view of an engine intake manifold having apertures to receive the EGR probe.
Figure 10:
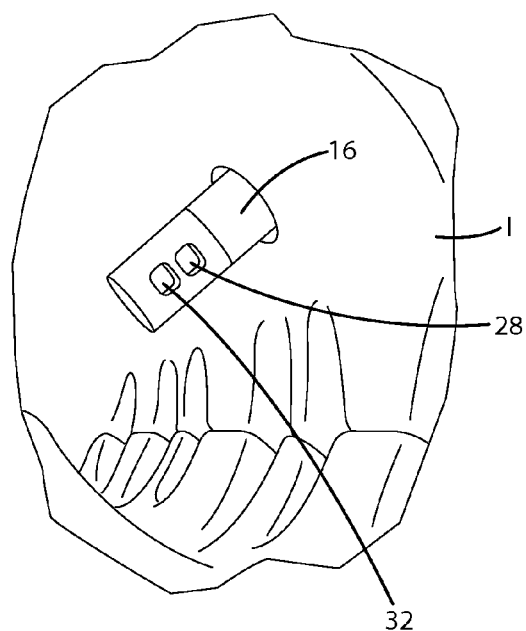
FIG. 10 is a perspective view of the EGR probe within the intake manifold.

As summarized above, the present invention is described in connection with the measurement of $CO_2$ concentrations within an engine intake manifold I. For purposes of disclosure, the present invention is described in connection with a GM 1.9E, 4-cylinder, direct injection diesel engine with Bosch common rail fuel injection, variable geometry turbo, electronic EGR valve, an intake swirl actuator, and a full-pass Drivven control system. FIG. 9 shows an engine intake manifold I with four circular mounting ports (or apertures A)—one associated with each cylinder. The size, shape, configuration, number and location of apertures A may vary from application to application as desired. FIG. 10 shows the EGR probe mounted in the intake manifold I. As can be seen, the inner end of the EGR probe 16 may be positioned so that the flow cells 28 and 32 (described below) are located at the location where samples are to be taken. The intake manifold apertures A are capable of receiving an EGR probe 16 manufactured in accordance with an embodiment of the present invention. In this embodiment the probe 16 is mounted to the intake manifold I via a standard bore-through SwageLok tube union boss, and positioned via a nonswaging ferrule. The EGR probe 16 may be mounted using other hardware, if desired. Although shown in an intake manifold, the EGR probe 16 may be installed in essentially any other structure containing a fluid stream, such as an exhaust manifold (not shown) or exhaust line (not shown).

Figure 3:
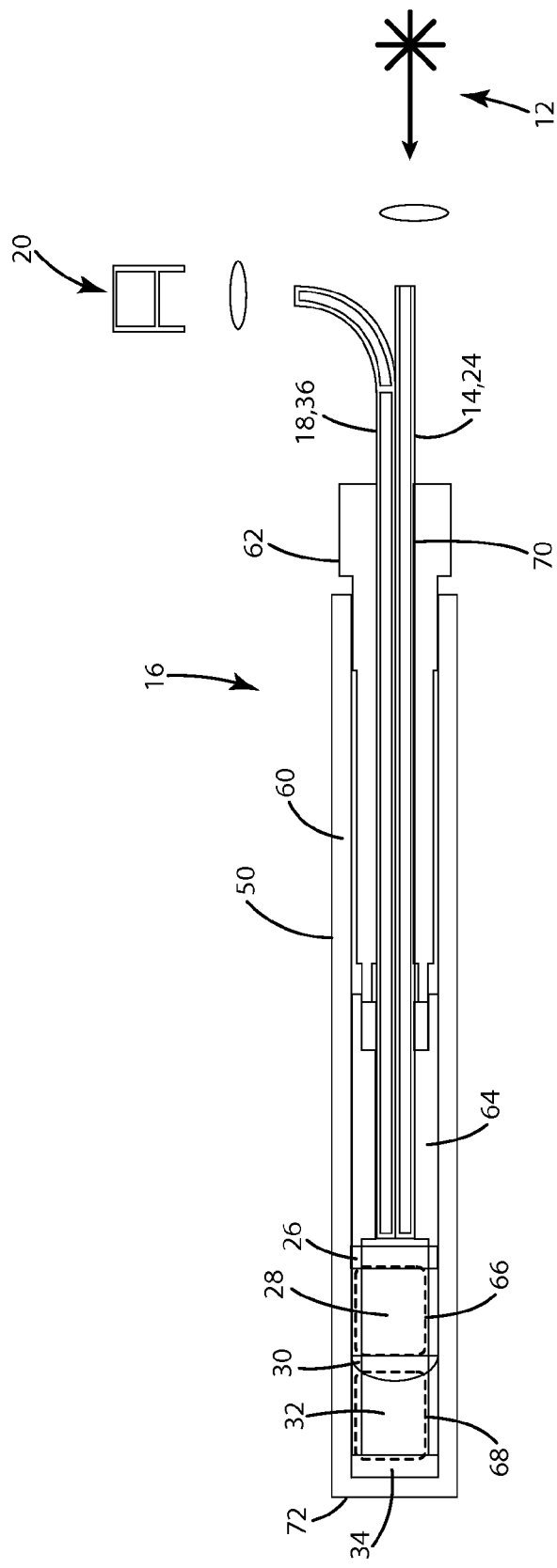
FIG. 3 is a schematic representation of the EGR probe, a light source and a detector.
Figure 4:
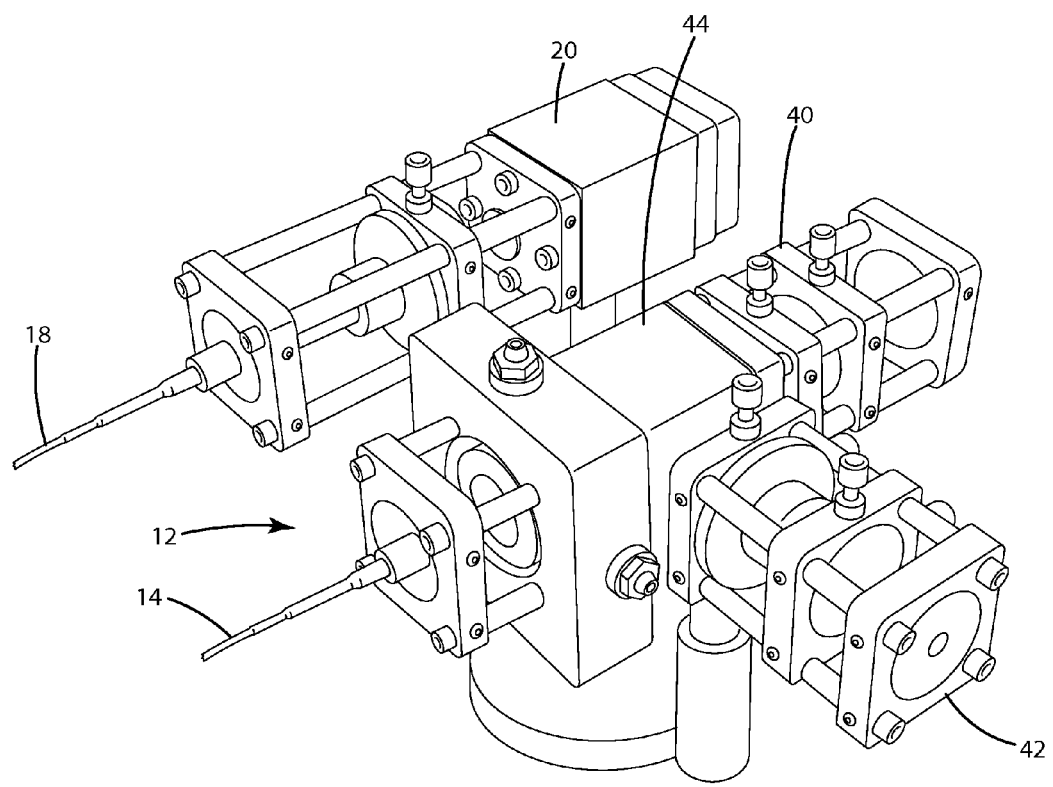
FIG. 4 is a perspective view of a combined light source and a detector.
Figure 5:
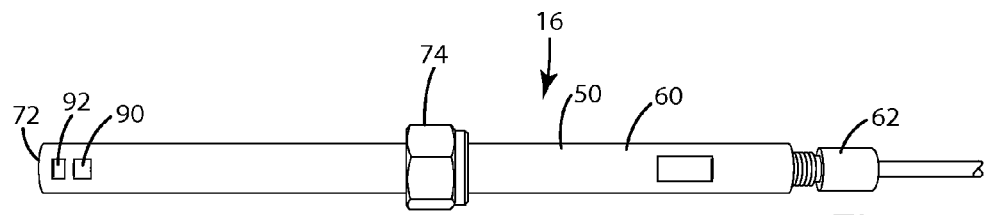
FIG. 5 is a side view of the EGR probe.
Figure 6:
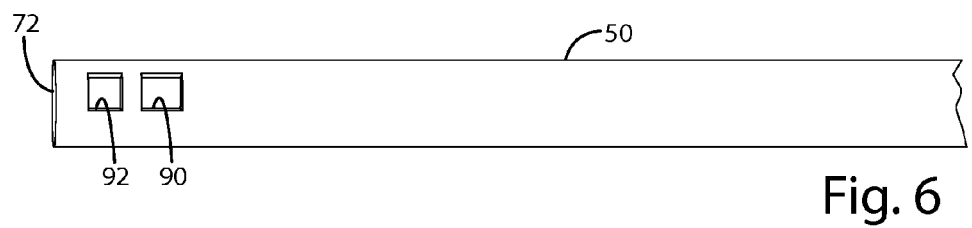
FIG. 6 is an enlarged side view of a portion of the EGR probe.
Figure 7:
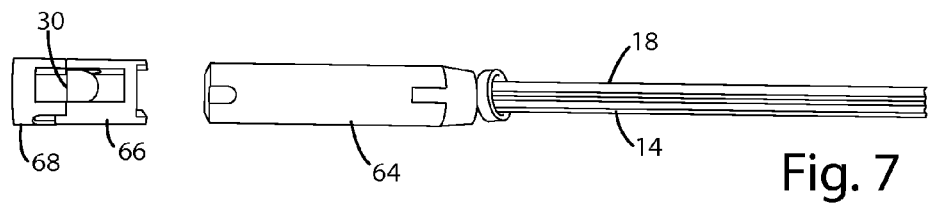
FIG. 7 is an enlarged side view of select subcomponents of the EGR probe.
Figure 8:
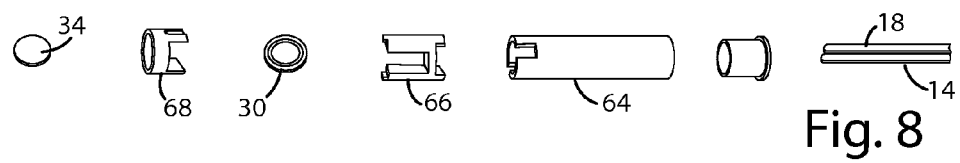
FIG. 8 is an exploded side view of select subcompoents of the EGR probe.

As noted above, FIG. 1 is a schematic representation of diagnostic system 10. As shown, the diagnostic system 10 of FIG. 1 generally includes a light source 12, a pitch optical cable 14, an EGR probe 16 with an internal sampling chamber 17, a catch optical cable 18, a detector 20 and a processor 22 for determining $CO_2$ concentration based on the output of the detector 20. The EGR probe 16 of the illustrated embodiment is a single-port probe capable of being installed in a single opening, such as aperture A in intake manifold I (See FIGS. 9-11). The EGR probe 16 of this embodiment includes a tubular housing 50 having a circular cross-section that corresponds with the shape of the aperture A in the intake manifold I. The housing 50 defines an internal void configured to define the sampling chamber 17 and to house the probe optics. In the illustrated embodiment, the sampling chamber 17 includes two separate flow cells (first flow cell 28 and second flow cell 32), and the probe optics are configured to direct the combined light beam through the flow cells. Referring now to FIG. 3, the probe optics of this embodiment include a pitch optical cable 24, a window 26, a lens 30, a mirror 34 and a catch optical cable 36. Pitch optical cable 14 and pitch optical cable 24 may be a single optical cable that extends from the light source 12 to the sampling chamber 17, or they may be separate optical cables that are joined together to form a continuous light path. Similarly, catch optical cable 18 and catch optical cable 36 may be a single optical cable that extends from the sampling chamber 17 to the detector 20, or they may be separate optical cables that are joined together to form a continuous light path. The housing 50 may include an outer tube 60, an inner tube 62, a mount 64, a first spacer 66 and a second spacer 68. In this embodiment, the outer tube 60 is approximately ⅜ of an inch in diameter and is configured to be fitted into a ⅜ of an inch diameter aperture A in the intake manifold I. The outer tube 60 is hollow and includes a closed inner end 72. As perhaps best shown in FIG. 6, the outer tube 60 defines sampling ports 90 and 92 that allow fluid from outside the EGR probe 16 to flow through the flow cells 28 and 32. The mirror 34, first spacer 66, lens 30, second spacer 68, window 26 and mount 64 are stacked within the hollow outer tube 60. The inner tube 62 may include an internal bore 70 configured to receive and support the pitch and catch optical cables. The inner tube 62 may be threadedly secured within the outer tube 60 to secure the various components of the EGR probe 16. A nut 74 may be fitted around the outer tube 60 for securing the EGR probe 16 is an aperture A. For example, the nut 74 may be a Swagelok nut. If desired, the EGR probe 16 may utilize a nonswaging ferrule to allow translation. The size, shape and configuration of EGR probe 16 is merely exemplary, and the EGR probe may vary from application to application. For example, the size, cross-sectional shape and internal configuration of the housing 50 may vary depending on the application. Similarly, the optical components may also vary depending on the application.

Figure 12:
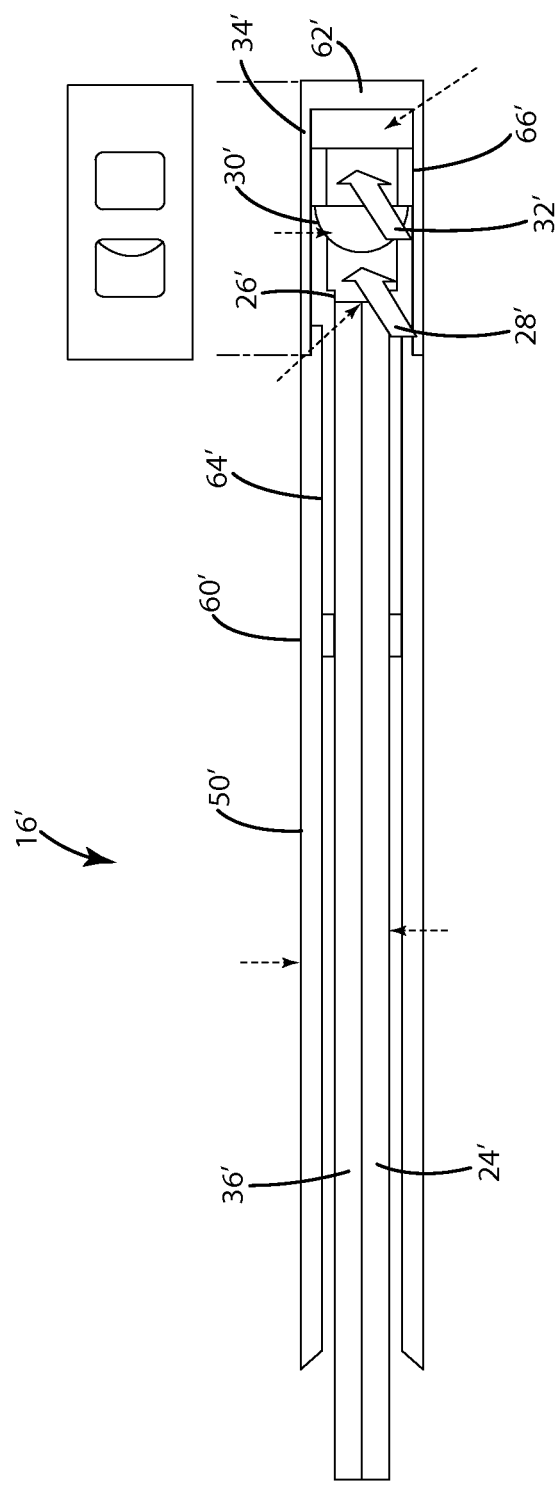
FIG. 12 is a schematic representation of an alternative embodiment of the EGR probe.

An alternative EGR probe 16' is shown in FIG. 12. In this embodiment, the EGR probe 16' is generally identical to EGR probe 16, except as described. As shown, EGR probe 16' includes essentially the same optics as EGR prober 16 having pitch and catch optical cables 24' and 36', window 26', first flow cell 28', lens 30', second flow cell 32' and mirror 34'. However, in this embodiment, the housing 50' is somewhat different having a main tube 60' and an end tube 62' that are joined end to end and cooperatively form an internal void to contain the probe optics and supporting structures. The main tube 60' and end tube 62' may be welded together or other joined as desired. The housing 50' includes a mount 64' that is fitted into the main tube 60' and the end tube 62'. The mount 64' may be threaded or otherwise secure to main tube 60' and/or the end tube 62'. The housing 50' also includes a spacer 66' that is fitted into the end tube 62' where it is disposed between the mirror 34' and the lens 30'.

Figure 2A:
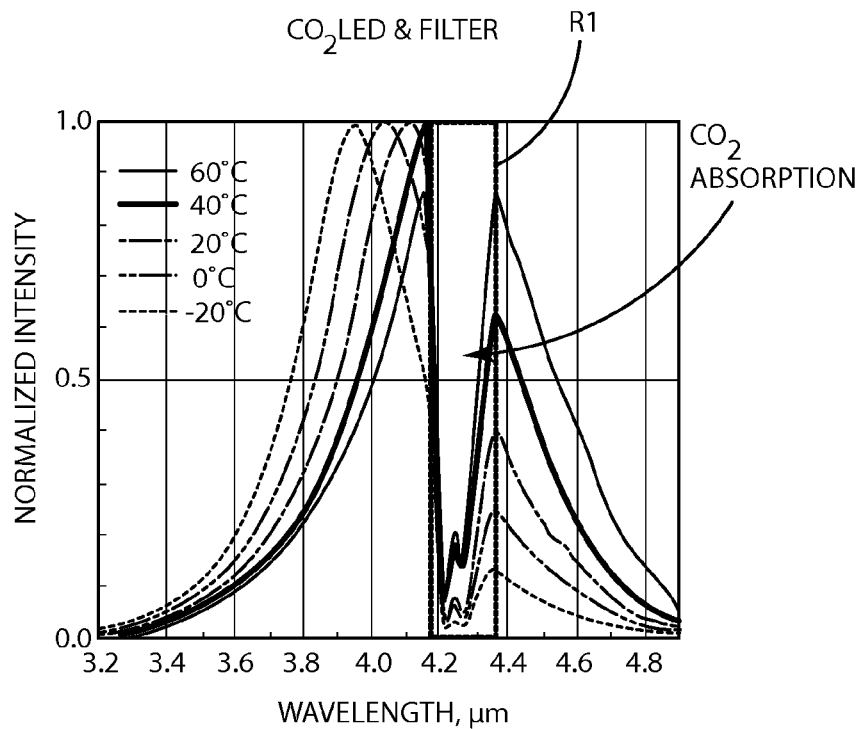
FIG. 2A is an emission spectra profile for a signal light source with a highlighted region showing the region where $CO_2$ absorbs light.
Figure 2B:
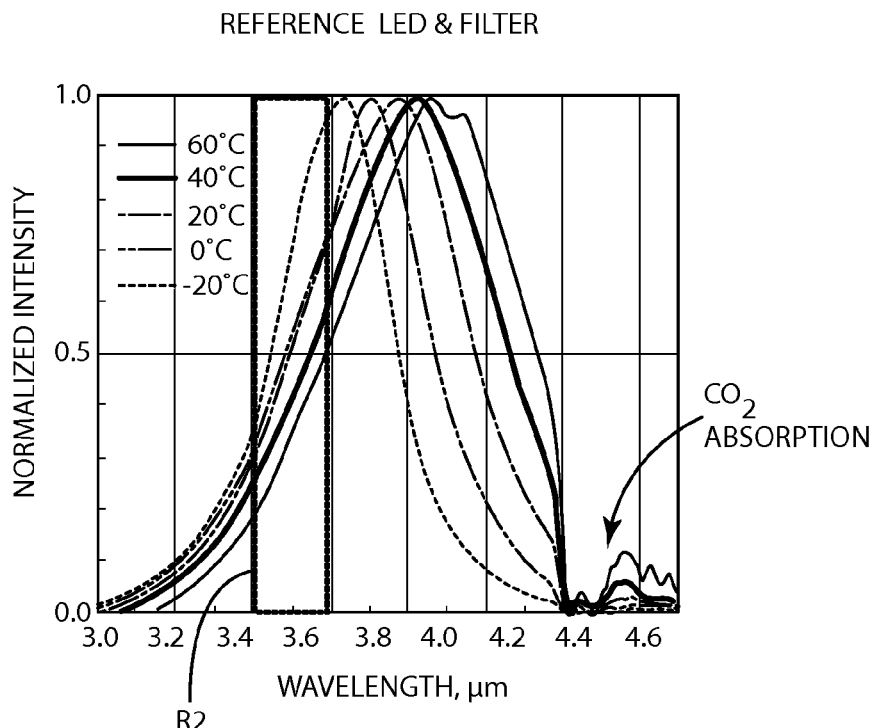
FIG. 2B is an emission spectra profile for a reference light source with a highlighted region showing a region where $CO_2$ does not absorb light effectively.

In the illustrated embodiment, the EGR probe 16 is intended for use with a light source 12 that produces light in the mid-infrared (MIR) range. This spectral range includes $CO_2$ absorption features that are sufficient to allow accurate measurement of $CO_2$ concentration. With a MIR light source, the pitch optical cable 24 and the catch optical cable 36 may be hollow waveguides configured for use in conveying MIR light. Hollow waveguides may provide improved light transmission as compared to other types of optical fibers or light guides. In the illustrated embodiment, the light source 12 is a combined light source that includes light produced by a signal source 40 and a reference source 42. In this embodiment, the EGR probe 16 is intended for use in measuring $CO_2$ concentration. As a result, the signal source 40 may be an MIR LED that produces light over a spectral range that is centered at 4.2 μm and overlaps the $CO_2$ absorption features near 4.3 μm. The characteristics of the signal source 40 may vary, for example, depending on the substance to be detected. The reference source 42 may be an MIR LED that produces light over a spectral range that is centered at 3.8 μm and does not coincide with $CO_2$ absorption features or other known interference species. The output of each light source 40, 42 may be spectrally filtered as shown in FIGS. 2A and 2B to provide the desired light beam. FIG. 2A shows the spectral range R1 of the filtered signal light source. FIG. 2B shows the spectral range R2 of the filtered reference light source. With this configuration, the reference source 42 may be used by the processor 22 to normalize the measurements of the signal source 40 taken by the detector 20.

The spectrally-filtered output of the signal source 40 and the spectrally-filtered output of the reference source 42 are combined, for example, using a beam combiner 44. The beam combiner 44 may be essentially any beam combiner or beam combiner/splitter capable of combining the light produced by the signal source 40 and the light produced by the reference source 42 into a composite light beam. The combined light beam is conveyed to the EGR probe 16 by pitch optical cable 14 and pitch optical cable 24. The light is output from the pitch optical cable 24 through window 26 into first flow cell 28. After passing through first flow cell 28, the light passes through lens 30 and second flow cell 32. The light then reflects off of mirror 34 and passes back through second flow cell 32, lens 30, first flow cell 28 and window 26. The mirror 34, lens 30 and window 26 are configured so that the returning light is directed into catch optical cable 36. Catch optical cable 36 conveys the light to catch optical cable 18. Catch optical cable 18 conveys the light to detector 20.

In this embodiment, the signal and reference light sources are driven at different modulation frequencies, such as 50 kHz and 77 kHz. These particular modulation frequencies are merely exemplary and the modulation frequencies may vary from application to application. In practice, it is desirable for the modulation frequencies to be sufficiently distant from one another so that the signals can be adequately separated by the processor 22. In the illustrated embodiment, the signal light source 40 is operated by a signal driver 80 that modulates the signal light source 40 at 50 kHz, and the reference light source 42 is operated by a reference driver 82 that modulates the reference light source at 77 kHz. The drivers 80 and 82 may be enabled by the processor 22, as shown in FIG. 1. This configuration is merely exemplary and the light sources may be driven using other electronic controls. For example, the processor 22 may be capable of directly driving the two light sources, 40 and 42, at the desired modulation frequencies.

The detector 20 may be essentially any photodetector capable of producing signals representative of the light beam returned from the EGR probe 16. The output of the detector 20 is connected to processor 22. The processor 22 may be essentially any processor capable of analyzing the detector output to provide $CO_2$ measurements. As noted above, the light beam passed through the EGR probe 16 is a combined light beam that is a composite of the light produced by the signal source 40 and the reference source 42. The processor 22 is configured to separate the combined light beam into a signal component and a reference component. In this embodiment, the signal component and reference component are resolved from the detector output using a Fourier transform. The processor 22 is also configured to normalize the signal component using the reference component. Given that the reference source is selected to include a spectral range that does not include any significant $CO_2$ absorption features, the reference component can be used to provide a base line for normalizing the signal component. The processor 22 is also configured to determine the $CO_2$ concentration in the fluid stream from the normalize signal component. The $CO_2$ concentration may be determined using conventional absorption spectroscopy methodologies.

Method of Use.

As noted above, the diagnostic system 10 is described in the context of an engine diagnostic tool. In this application, the diagnostic system 10 may be used to measure $CO_2$ concentrations within an engine intake manifold to determine spatial and temporal nonuniformities of $CO_2$ in the fluid stream. For example, the system 10 may be used to measure cylinder-to-cylinder and cycle-to-cycle $CO_2$ fluctuations. In the context of engines with exhaust gas redistribution (EGR), the $CO_2$ measurements taken by the diagnostic system 10 may be used to quantify intake EGR fluctuations. The data collected by the diagnostic system 10 may be used simply to characterize performance, or it may be used to refine the EGR system, the intake manifold I, engine control parameters or other characteristics to improve performance of the engine and minimize $NO_X$ production.

In the illustrated embodiment, the diagnostic system 10 is used to measure $CO_2$ concentrations within an engine intake manifold I. The engine intake manifold I includes a plurality of apertures A that allow the EGR probe 16 to be selectively installed in the intake manifold I at different locations. In the illustrated embodiment, the intake manifold I has four apertures A—one associated with each cylinder. As noted above, the EGR probe may be secured within an aperture A using a conventional Swagelok union. Sealant may be used to reduce the potential for leaking around the union. The number and location of the apertures may vary from application to application. In this application, the EGR probe 16 may be used to assess spatial and temporal fluctuations in $CO_2$ concentrations. For example, the EGR probe 16 may measure the $CO_2$ concentrations at various locations within the intake manifold to determine the spatial uniformity of exhaust gas recirculation. For this purpose, the present invention may use a single EGR probe 16 that may be moved from time to time to measure $CO_2$ concentrations at different locations. In one embodiment, the EGR probe 16 may be used to measure the $CO_2$ concentrations at each cylinder to assess the cylinder-to-cylinder uniformity of recirculated exhaust gas. As an alternative to a single probe 16, the system 10 may include a plurality of EGR probes 16 that allow simultaneous measurements from different locations within the manifold. In some application, a separate diagnostic system may be used for each location, and the output of the different systems may be compared to assess the differences.

As an alternative to measuring spatial uniformity, the EGR probe 16 may measure the $CO_2$ concentrations at a given location over time to determine changes in $CO_2$ concentration over time. In this application, the temporal differences may be determined to assess cycle-to-cycle uniformity of the EGR system. A single EGR probe 16 may be used to measure $CO_2$ concentrations at a single location over time, or a plurality of EGR probes may be used to simultaneously measure $CO_2$ concentrations at different locations. As an alternative to cycle-to-cycle measurements, the present invention may be used to take measurements at essentially any timescale (e.g. individual valve events, or intra-valve events, or longer term drift or variations). The diagnostic system 10 may be used to perform other types of diagnostics that depend on $CO_2$ concentration or the concentration of other substances that may be measured using the present invention.

In one application, the method generally includes the steps of: (a) providing an EGR probe 16 in which the pitch and catch optical path are includes in a single housing suitable for mounting within a single port, (b) producing a signal light beam and a reference light beam over different spectra, (c) combining the signal and reference light beams into a combined light beam, (d) directing the combined light beam in a first direction through the housing via a pitch cable, (e) passing the combined light beam from the pitch cable through the fluid stream to be measured (e.g. a portion of the intake or exhaust manifold), (f) reflecting the combined light toward a catch cable, (g) directing the reflected beam through the housing in a direction opposite to the first direction via a catch cable, (h) receiving the light beam at a detector, and (i) determining the concentration of a component within the intake or exhaust manifold as function of the detected light beam.

In this embodiment, the signal light source and reference light source are modulated at different frequencies (e.g., 50 kHz and 77 kHz, respectively) so that they can be separated from the detector signals. For example, the signal and reference components of the combined light beam can be separated by processor 22 using a Fourier transform. In this embodiment, the signal light source and reference light source may be modulated using separate drivers, such as signal driver 80 and reference driver 82.

In the illustrated embodiment, the signal and reference light beams are combined into a single light beam using a beam combiner/splitter. The beam combiner may be essentially any beam combiner or beam splitter capable of combining the MIR output of the signal and reference light sources into a single composite light beam.

Figure 11:
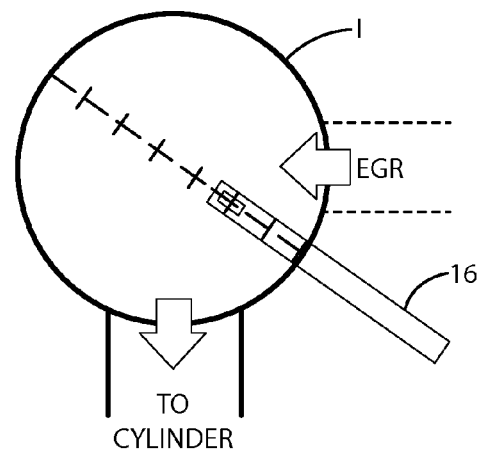
FIG. 11 is a schematic representation of the EGR probe within the intake manifold illustrating the adjustability of the depth of the probe.

When measuring spatial fluctuations with a single probe, the method may also include the steps of (a) installing the EGR probe 16 in a first location in the intake manifold I, (b) taking $CO_2$ measurements at the first location, (c) installing the EGR probe 16 in a second location, (d) taking $CO_2$ measurements at the second location and (e) repeating these steps for each additional location to be measured. The location may be varied by moving the EGR probe 16 from one aperture A to another and/or by varying the depth of EGR rpobe 16 within an aperture A. FIG. 11 is a schematic representation of the EGR probe 16 in the intake manifold I. The depth of the EGR probe 16 within the intake manifold I can be adjusted to essentially any location along line L.

When measuring spatial fluctuations with a plurality of probes, the method may also include the steps of (a) installing a separate EGR probe 16 in each desired location within the intake manifold I and (b) simultaneously taking $CO_2$ measurements at each location using the separate EGR probes 16.

When measuring temporal fluctuations, the EGR probe 16 or EGR probes 16 may be installed in the desired location(s) in the engine intake manifold I and a plurality of measurements may be taken over time. The number of measurements and the timing between measurements vary from application to application, as desired.

The measurements produced by the detector 20 are processed by processor 22 to determine the concentration of $CO_2$. This process may include the steps of: (a) separating the detector measurements into a signal component and a reference component; (b) normalizing the signal component using the reference component and (c) determining the $CO_2$ concentration from the normalized signal component. The step of separating the detector measurements into a signal component and a reference component may include processing the measurements using a Fourier transform that separates the components based on their different modulation frequencies. Such processing also minimizes the effect of detector noise on the measurement precision. The step of normalizing the signal component may include adjusting the signal component as a function of the reference component. Once the signal component has been normalized, the $CO_2$ concentration may be determined using conventional absorption spectroscopy methodologies, which will not be described in detail here.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The invention claimed is:

1. An apparatus for determining $CO_2$ concentrations in a fluid stream, the apparatus comprising:
   a combined light source affixed to a first end of an pitch optic cable, the combined light source having a probe LED producing light in a first portion of the MIR spectrum including significant $CO_2$ absorption features; and a reference LED producing light in a second portion of the MIR spectrum not including significant $CO_2$ absorption features;
   a lens disposed proximate a second end of the pitch optic cable for directing the combined light source through a sampling chamber to a mirror;
   a catch optic cable having a second end disposed proximate said lens; and
   a catch optic affixed to a first end of said catch optic cable.

2. The apparatus of claim 1 wherein the concentration of $CO_2$ is determined by the level of probe LED light detected by said catch optic.

3. The apparatus of claim 1 wherein said combined light source includes a signal source and a first spectral filter producing light over a portion of the MIR spectrum including 4.2 μm and a reference source and a second spectral filter producing light over a portion of the MIR spectrum including 3.8 μm.

4. The apparatus of claim 3 wherein said signal source and said reference source are modulated at different frequencies.

5. The apparatus of claim 4 further including a detector configured to receive a light beam from said catch optic cable and to produce detector signals representative of the light beam.

6. The apparatus of claim 5 further including a processor for analyzing said detector signals to obtain $CO_2$ measurements of a fluid in the said sampling chamber.

7. The apparatus of claim 6 wherein said processor is configured to separate a reference component and a signal component from said detector signals, and to normalize said signal component using said reference component.

8. The apparatus of claim 6 wherein said processor is configured to separate a reference component and a signal component from said detector signals by a Fourier transform, and to normalize said signal component using said reference component.

9. A diagnostic system comprising:
   a signal light source producing light in a first portion of the MIR spectrum, said first portion including $CO_2$ absorption features;
   a reference light source producing light in a second portion of the MIR spectrum, said second portion not including substantial $CO_2$ absorption features;
   a beam combiner disposed adjacent to said signal light source and said reference light source to produce a combined light beam;
   a detector for producing measurements representative of a light beam; and
   a probe including:
      a single port housing;
      a sampling chamber defined within said housing;
      a pitch optical cable disposed within said housing, said pitch optical cable conveying said combined light beam from said beam combiner to said sampling chamber;
      a catch optical cable disposed within said housing, said catch optical cable conveying said combined light beam from said sampling chamber to said detector;
      a mirror disposed adjacent said sampling chamber for reflecting said combined light beam to said catch optical cable.

10. The system of claim 9 further including a signal driver for modulating said signal source at a first frequency, and a reference driver for modulating said reference source at a second frequency different from said first frequency.

11. The system of claim 10 further including a processor for processing said measurements produced by said detector, said processor configured to separate a reference component and a signal component from said detector measurements as a function of said first frequency and said second frequency, and to normalize said signal component using said reference component.

12. The system of claim 11 wherein said processor is configured to separate said reference component and signal component using a Fourier transform.

13. The system of claim 12 wherein said sampling chamber includes a first flow cell and a second flow cell arranged in series along a light path from said pitch optical cable to said mirror and from said mirror to said catch optical cable, whereby said combined light beam passes through each of said flow cells twice as it travels from said pitch optical cable to said catch optical cable.

14. The system of claim 13 wherein said probe include a lens disposed between said first flow cell and said second flow cell.

15. The system of claim 14 wherein said probe includes a window disposed between said first flow cell and said pitch optical cable.

16. A method for quantifying EGR fluctuations, comprising the steps of:
   providing an EGR probe in which pitch and catch optical paths are included in a single housing suitable for mounting within a single port;
   producing a signal light beam and a reference light beam over different spectra;
   combining the signal and reference light beams into a combined light beam;
   directing the combined light beam in a first direction through the housing via a pitch cable;
   passing the combined light beam from the pitch cable through a fluid stream to be measured;
   reflecting the combined light toward a catch cable;
   directing the reflected beam through the housing in a direction opposite to the first direction via a catch cable;
   receiving the light beam at a detector; and
   determining with a processor the concentration of a component within an intake or exhaust manifold as a function of the detected light beam.

* * * * *